United States Patent [19]

Richardson

[11] Patent Number: 5,372,134
[45] Date of Patent: Dec. 13, 1994

[54] AVIATION HYPOXIA MONITOR

[76] Inventor: Joseph W. Richardson, 229 Desha, Lexington, Ky. 40502

[21] Appl. No.: 66,790

[22] Filed: May 24, 1993

[51] Int. Cl.$^5$ .............................................. A61B 5/00
[52] U.S. Cl. ................................................... 128/633
[58] Field of Search ............... 128/632, 633, 664, 665; 356/41

[56] References Cited

U.S. PATENT DOCUMENTS

| H1039 | 4/1992 | Tripp, Jr. et al. ............ 128/633 |
|---|---|---|
| 4,321,930 | 3/1982 | Jöbsis et al. ................ 128/633 |
| 4,510,938 | 4/1985 | Jöbsis et al. ................ 128/633 |
| 4,621,643 | 11/1986 | New, Jr. et al. . |
| 4,653,498 | 3/1987 | New, Jr. et al. . |
| 4,700,708 | 10/1987 | New, Jr. et al. . |
| 4,802,486 | 2/1989 | Goodman et al. . |
| 4,869,254 | 9/1989 | Stone et al. . |
| 4,926,867 | 5/1990 | Kanda et al. ................ 128/633 |
| 4,968,137 | 11/1990 | Yount ............................ 356/41 |
| 5,007,423 | 4/1991 | Branstetter et al. ........... 128/633 |
| 5,080,098 | 1/1992 | Willett et al. ................ 128/633 |
| 5,131,391 | 7/1992 | Sakai et al. . |

Primary Examiner—Lee S. Cohen
Assistant Examiner—Samuel Gilbert

[57] ABSTRACT

A hypoxia monitor is incorporated into the headphones worn by a pilot. The hypoxia monitor is preferably a pulse oximeter which provides a noninvasive monitoring of blood levels of the pilot. The pulse oximeter probe is mounted on the ear seal of the headphone so that it contacts the skin beneath the ear of the pilot. The probe is wired through the headphone wires and attaches to a monitor mounted in the panel of the airplane. The monitor provides a visual and audio signal if the blood level of the pilot decreases significantly. This will alert the pilot to either reduce his altitude or provide additional oxygen for the cockpit area.

10 Claims, 1 Drawing Sheet

AVIATION HYPOXIA MONITOR

BACKGROUND OF THE INVENTION

Hypoxia is a deficiency of blood reaching tissues and organs of the body which is generally associated with a drop in the blood oxygen level. When hypoxia occurs, the individual becomes disoriented and confused. An extreme loss of oxygen over a sufficient period of time will cause the individual to become unconscious.

This is a severe problem with pilots. If a pilot becomes disoriented or unconscious for even a very brief period of time, a crash can occur. Hypoxia is a particularly significant problem with pilots because of the decrease in oxygen level at higher altitudes. If a pilot breathes ambient air, at a sufficiently high altitude, the loss of oxygen in the ambient air can cause hypoxia. A second cause of hypoxia call be breathing exhaust from the airplane engine. Although airplanes are certainly designed to prevent engine exhaust from entering the cockpit area, this can occur. The carbon monoxide contained in such gases will enter the blood stream and prevent oxygenation of the blood, and thus, a decrease in blood oxygen level.

In the past, there have been invasive methods used to monitor blood oxygen levels of astronauts. However, invasive methods are unsuitable for pilots. Any system for pilots must be noninvasive and very simple to operate.

SUMMARY OF THE INVENTION

It is accordingly an object of the present invention to provide a noninvasive hypoxia detection system for pilots. Further, it is an object of the present invention to provide such a system which is automatically and accurately applied to the pilot's body without requiring any additional steps or work by the pilot. Further, it is an object of the present invention to provide such a monitor which does not restrict the movement to the pilot and does not have dangling wires which could also interfere with the movement of the pilot.

The objects and advantages of the present invention are provided by measuring blood oxygen levels using a noninvasive hypoxia monitor attached to the skin of a pilot. More particularly, the present invention is provided by mounting such a noninvasive hypoxia sensor to the headphones of the pilot, such that when the pilot puts on the headphones, the hypoxia sensor will be located in a position which will permit it to accurately measure the oxygen level of the pilot.

Preferably, the hypoxia monitor is integral with the pilot's headphones and has its wiring running with the wiring of the headphones so that the hypoxia monitor can be plugged into a monitor in the panel of the airplane alongside the terminals for the headphone plug. Alternately, the headphone can employ one multi-prong plug with several of the prongs dedicated to the hypoxia monitor.

The hypoxia monitor itself can be either a stand alone unit or can be incorporated into added components of the airplane such as the flight management system.

The objects and advantages of the present invention will be further appreciated in light of the following detailed description and drawings in which:

DETAILED DESCRIPTION

Figure 1:
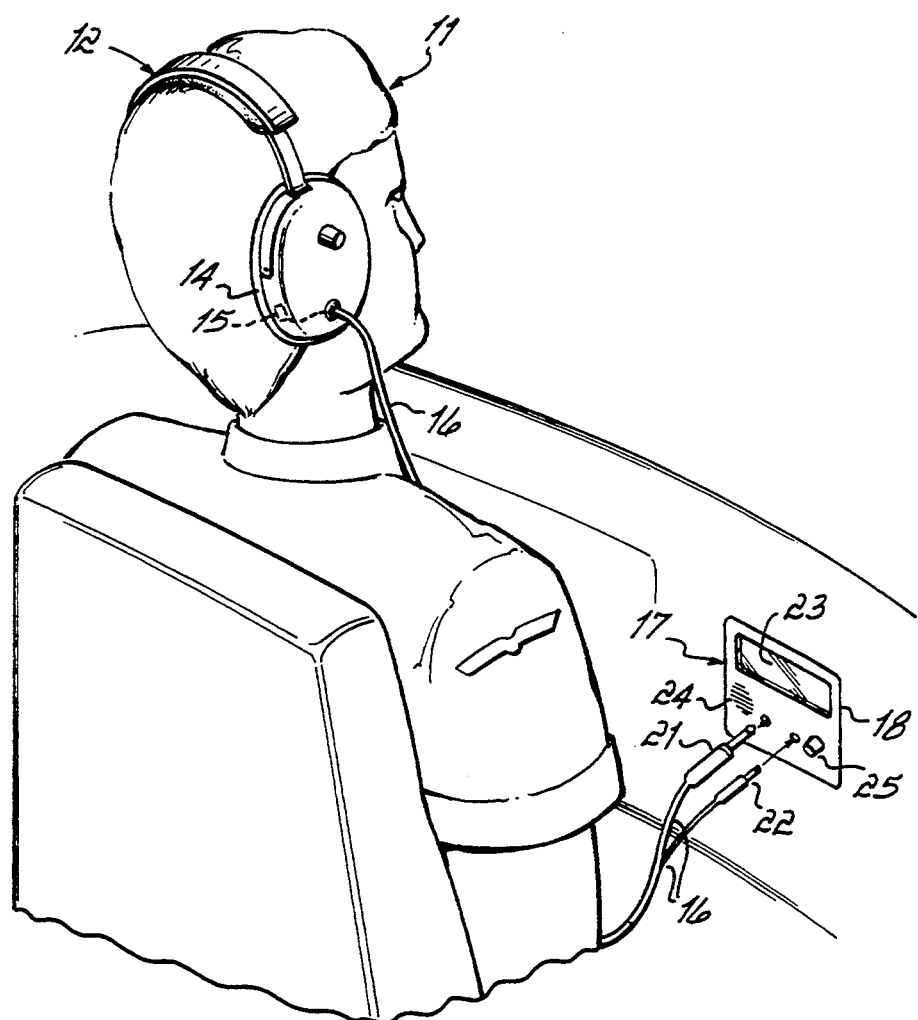
FIG. 1 is a diagrammatic depiction of the present invention in use.

The present invention provides a method of measuring the oxygen level of the blood of a pilot flying an airplane. As shown in FIG. 1, the pilot 11 is wearing headphones 12 which has a left ear seal 13 and a right ear seal 14. Mounted on the right ear seal 14 is a blood oxygen level sensor 15. Extending from the left and right ear seals 13, 14 are the headphone wires 16. These extend to a monitor 17 mounted in the panel 18 of the airplane. As shown, the monitor 17 includes two female connections, the headphone connections 21 and the oxygen monitor connection 22.

The oxygen monitor includes a visual display 23 and a speaker 24 to provide audio output. Likewise, there is shown a control 25 to adjust the blood oxygen level at which the audio and visual display will provide a warning as is described below.

As shown in FIG. 1, the sensor 15 is preferably located in the lower half of the right ear seal 14. In this position, the monitor should rest on the pilot's skin and not on his hair. A pilot with longer hair may have to brush his hair back to ensure that the sensor contacts the skin.

Figure 2:
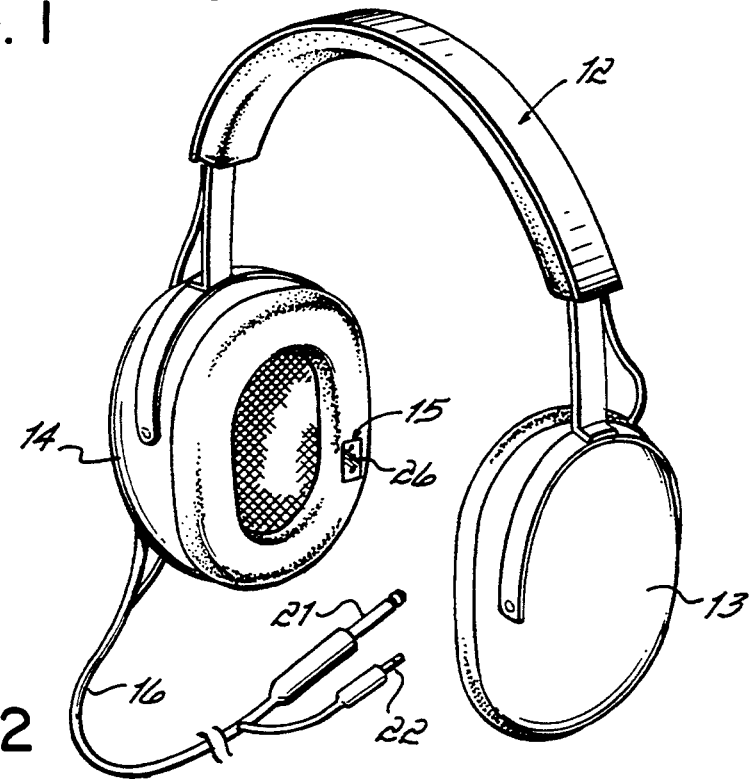
FIG. 2 is a perspective view of a headphone incorporating a hypoxia monitor according to the present invention.

The sensor can be attached to the ear seal in various ways. As shown in FIG. 2, the sensor 15 is held in a clear plastic envelope 26 affixed to ear seal with a pressure sensitive adhesive (not shown). Wires connecting the sensor to the monitor 17 run through the ear seal 14 and subsequently run alongside the wiring 16 for the headphones up to the airplane's panel 18.

The wires 16 can also run around the exterior of the ear seal. The sensor can also be molded into the ear seal. In this embodiment, the sensor would be replaced by replacing the ear seal.

With respect to the oxygen sensor 15, any oxygen sensor which is noninvasive and merely functions by measuring oxygen level through the skin of the pilot 11 will be acceptable for use in the present invention. A preferred monitor is a pulse oximeter.

There are a variety of such sensors. For example, Sakai et al. U.S. Pat. No. 5,131,391 discloses a suitable pulse oximeter. Likewise, New, Jr. et al. U.S. Pat. No. 4,653,498, New, Jr. et al. U.S. Pat. No. 4,700,708, New, Jr. et al. U.S. Pat. No. 4,770,179, Goodman et al. U.S. Pat. No. 4,802,486, Stone et al. U.S. Pat. No. 4,869,254, and New, Jr. et al. U.S. Pat. No. 4,621,643 disclose suitable oximeters and probes which could be incorporated in the present invention. Preferred pulse oximeters are manufactured and sold by Nellcor Incorporated of Haywood, Calif. These are the N-100 oximeter and the N-200 oximeter.

For example, the N-100 oximeter sold by Nellcor Incorporated is a microprocessor controlled device that measures oxygen saturation of hemoglobulin using light from two light emitting diodes (LEDs), one having a discrete frequency of about 660 nanometers in the red light range and the other having a discrete frequency of about 925 nanometers in the infrared range. The N-100 oximeter microprocessor uses a four state clock to provide a five polar drive circuit for the two LEDs so that a positive current pulse drives the infrared LED and a negative current pulse drives the red LED to illuminate alternately the two LEDs so that the incident light will pass through the skin which the probe is contacting and the transmitted light will be detected by a single photo detector.

The clock uses a high strobing rate, for example, 1500 cycles per second, to be easily distinguished from other light sources. The photo detector current changes in response to the red and infrared light transmitted in sequence and is converted to a voltage signal, amplified and separated by a two-channel synchronous detector—one channel for processing the red light wave form and the other channel for processing the infrared light wave form. The separated signals are filtered to remove the strobing frequency, electrical noise, and ambient noise and then digitized to an analog to digital converter. As used herein, the incident light and the transmitted light refers to the light generated by the LED or other light source as distinguished from ambient or environmental light.

The light source intensity may be adjusted to accommodate variations among patient's skin color, flesh, thickness, hair color, blood, and other variants. The light transmitted is thus modulated by the absorption of light in the variants, particularly the arterial blood pulse or pulsatile component, and is referred to as the plethysmograph waveform or the optical signal. The digital representation of the optical signal is referred to as the digital optical signal. The portion of the digital optical signal that refers to the pulsatile component is labeled the optical pulse.

The detected digital optical signal is processed by the microprocessor of the N-100 oximeter to analyze and identify optical pulses corresponding to arterial pulses and develop a history as to pulse periodicity, pulse shape, and determine oxygen saturation. The N-100 oximeter microprocessor decides whether or not to accept a detected pulse as corresponding to an arterial pulse by comparing the detected pulse against the pulse history. To be accepted, the detected pulse must meet certain predetermined criteria. For example, the expected size of the pulse, when the pulse is expected to occur, and the expected ratio of the red light to infrared light of the detected optical pulse in accordance with the desired degree of confidence. Identified individual optical pulses accepted for processing are used to compute the oxygen saturation from the ratio of maximum and minimum pulse levels as seen by the red wave length compared to the maximum and minimum pulse levels as seen by the infrared wave length.

Normally, the relative oxygen content of the individual's arterial pulse remains about the same from pulse to pulse and the average background absorption between the pulses remains about the same. Consequently, the red and infrared light that is transmitted through the pulsatile flow produces a regularly modulated plethysmograph wave form having periodic optical pulses of comparable shape and amplitude and a steady state background transmittance. This regular pulse provides for an accurate determination of oxygen saturation of the blood based on the detected relative maximum and minimum transmittance of red and infrared light.

Although the Nellcor monitor is preferred, other pulse oximeters can also be employed. This technology is very well developed and one skilled in the art can select from commercially available pulse oximeters to incorporate into the present invention.

In operation, the oxygen sensor 15, which is part of the ear seal 14, is put into contact with the pilot's skin beneath his ear when the pilot puts on the headphones. This forces the sensor 15 into close contact with the skin of the pilot. The ear seal 14 also shields light from the sensor so that only light emitted from the light emitting diodes will be picked up by the sensor 15. The headphones are then plugged into the instrument panel and the oxygen sensor is attached to the oxygen monitor connection 22. The threshold at which the alarm will sound can be adjusted by adjusting the monitor using control 25 which adjusts the random access memory of the monitor preventing activation of the alarm until the pilot's oxygen level reaches a certain defined degree of desaturation. Typically, this will be in the range of 90 to less than about 100%. This permits the monitor to compensate for skin color and hair as well as physiological factors such as the smoking habits of the pilot.

Alternately, the monitor can be programmed so that a percentage change in the pilot's oxygen saturation level will cause an alarm to be sounded. This will inherently compensate for different metabolisms.

Once the pilot is in the plane and the monitor is functioning, should the pilot's oxygen level reach a critical level, the alarm will sound alerting the potentially disoriented pilot and advise him by visual display to descend to a lower altitude or to add oxygen to the cockpit. This will enable the pilot to take corrective measures before a crash occurs.

There are, of course, many variations and modifications which can be made. For example, the oxygen sensor was simply described as mounted to the ear seal of the headset. This obviously can be modified to provide for easy removal and replacement of the sensor. In a less preferred embodiment, the sensor could be taped on to the pilot's body, for example, on his neck or the like.

With these obvious variants of the invention in mind, the invention itself should only be defined by the appended claims wherein I claim:

1. A hypoxia detection system for an airplane pilot comprising, headphones having at least one ear seal adapted to be positioned around an ear of a pilot; and
   said headphones further including a noninvasive blood oxygen saturation sensor mounted on said at least one ear seal, said sensor adapted to be pressed against skin of said pilot when said headphones are on a head of said pilot;
   wherein said sensor is adapted to be connected to a blood oxygen saturation monitor.

2. The system claimed in claim 1 wherein said oxygen sensor is located in a lower half of said ear seal.

3. The system claimed in claim 1, further including audio wiring adapted to plug into a panel of an airplane and wherein said sensor is connected to sensor wiring having an output plug wherein said sensor wiring runs along said audio wiring.

4. The system claimed in claim 3 in combination with a monitor, said monitor connected to the output plug of said sensor.

5. The system claimed in claim 4 wherein said monitor is part of a flight navigation system.

6. The system claimed in claim 4 wherein said monitor incorporates an automatic audio warning, said automatic audio warning activated upon detection of a defined blood saturation limit of said pilot.

7. The system claimed in claim 6 wherein said monitor includes means for adjusting the defined blood saturation limit.

8. A method of monitoring a blood saturation limit level of a pilot comprising:

positioning a noninvasive oxygen saturation sensor between an ear seal of headphones and a pilot's skin and pressing said sensor against said skin;

measuring an oxygen level of said pilot detected by said sensor as said pilot wears said headphones, 9. The method claimed in claim 8 further comprising providing an audio alarm when said oxygen level of said pilot reaches a defined desaturation limit.

10. The method claimed in claim 9 further comprising manually establishing said defined desaturation limit.

* * * * *